United States Patent

Huber et al.

[11] Patent Number: 5,952,185
[45] Date of Patent: *Sep. 14, 1999

[54] PHOTO-ACTIVATABLE BIOTIN DERIVATIVES AND THEIR USE TO REDUCE INTERFERENCE IN IMMUNOASSAYS

[75] Inventors: Erasmus Huber, Finning; Michael Wiedmann; Frédéric Donié, both of Penzberg, all of Germany

[73] Assignee: Boehringer Mannheim GmbH, Mannheim, Germany

[*] Notice: This patent is subject to a terminal disclaimer.

[21] Appl. No.: 08/958,870

[22] Filed: Oct. 27, 1997

Related U.S. Application Data

[63] Continuation of application No. 08/535,072, Nov. 3, 1995, abandoned.

[30] Foreign Application Priority Data

Mar. 5, 1994 [DE] Germany ............................ 44 07 423

[51] Int. Cl.⁶ .................................................. G01N 33/543
[52] U.S. Cl. ........................ 435/7.5; 436/811; 436/825; 530/408; 530/807; 548/304.1
[58] Field of Search ...................... 548/304.1; 530/807, 530/408; 435/7.5; 436/811, 825

[56] References Cited

U.S. PATENT DOCUMENTS 5,395,938  3/1995  Ramakrishnan ..................... 546/104

FOREIGN PATENT DOCUMENTS 155854   9/1985  European Pat. Off. .
331068   9/1989  European Pat. Off. .
4302241  7/1994  Germany .

OTHER PUBLICATIONS

U. Henriksen et al., J. Photochemistry and Photobiology, vol. 57, pp. 331–342, 1991.

*Primary Examiner*—Mary E. Ceperley
*Attorney, Agent, or Firm*—Nikaido Marmelstein Murray & Oram LLP

[57] ABSTRACT

The invention addresses new photo-activatable biotin derivatives having the formula I

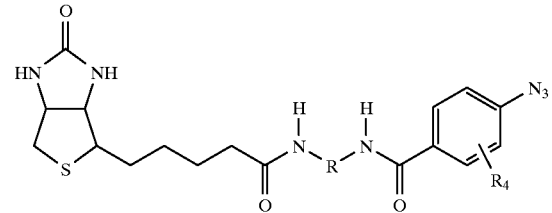

wherein $R=[(CH_2)_n—O_m]_q—[(CH_2)_r—O_s]_t—(CH_2)_p$ with n,r=2,3; m,s=0,1; q+t=1–4; p=1–4, wherein the sum of all $CH_2$ groups does not exceed 10 and wherein R1 as a single or multiple substituent is hydrogen, $C_1$–$C_5$alkyl, $NH_2$, COOH, F, Cl, or Br.

and their preparation, their use to inactivate streptavidin, the use of the inactivated streptavidin to reduce interference in immunoassays.

17 Claims, No Drawings

PHOTO-ACTIVATABLE BIOTIN DERIVATIVES AND THEIR USE TO REDUCE INTERFERENCE IN IMMUNOASSAYS

This application is a continuation of application Ser. No. 08/535,072, filed Nov. 3, 1995 now abandoned which is a 371 of PCT/EP95/00690, filed Feb. 25, 1995.

The invention addresses novel photo-activatable biotin derivatives, their preparation, their use to inactivate streptavidin or avidin, the use of the inactivated streptavidin to reduce interference in immunoassays, and a method for the detection of an analyte using the inactivated streptavidin.

Immunological detection methods have gained great importance over the last years. They serve to detect the presence of drugs, hormones, proteins, infectious organisms, and especially specific antibodies in biological samples in a rapid and exact manner. In all immunological detection methods, there occurs a specific binding reaction between a first specific binding partner, the substance to be detected (analyte) and a second specific binding partner which specifically reacts with the analyte and binds it. Analyte and specific analyte binding partner form a so-called specific binding pair generally a complex between antigen and an antibody or antibody fragment. It is possible to have more than one analyte or binding partner react with each other in each reaction. These specific binding reactions are detected in various ways. Generally, one participant in the specific binding reaction is labeled. Conventional labeling methods include radio-isotopes, chromogens, fluorogens, enzymatic labels or substances which in turn form another specific binding pair (e.g. biotin/streptavidin). In heterogeneous immunoassays, one of the binding partners is immobilized on a solid phase.

A difficult problem in immunoassays is that there may be undesired interactions and non-specific binding reactions between specific binding partners of the immunoassay and the sample, the additional components contained in said sample, and possibly the solid phase. These interactions generally lead to an increase in the background signal and a higher scattering of the signals which in turn reduces sensitivity and specificity of the test in question. Both non-specific interactions with the labeled binding partner and non-specific binding of test components and sample components can lead to false-positive results, i.e. the erroneous presence of an analyte is measured even when such an analyte is absent.

Various attempts have been made to reduce these non-specific interactions in immunoassays. It has been known for some time that various carbohydrate components and various proteins, protein mixtures, or protein fractions as well as their hydrolysates reduce non-specific interactions between test components and the analyte in immunoassays (e.g. Robertson et al., Journal of Immun. Meth. 26, 1985, 195; EP-A-260 903; U.S. Pat. No. 4,931,385).

The use of protein raw fractions and raw hydrolysates has the disadvantage that the contaminations contained therein may interfere with the test. Moreover, enzymatically produced hydrolysates could also be contaminated with proteases used for their preparation. Also, their quality is usually not uniform as the cleavage procedures are difficult to control. Protease contaminations can attack test components and even minute amounts may negatively affect the performance of the test and its stability.

The use of chemically modified proteins, especially succinylated or acetylated proteins has been described to reduce non-specific interactions in immunoassays (U.S. Pat. No. 5,051,956; EP-A-0 525 916). However, many of the false-positive results in tests for antibodies in the serum cannot be avoided with these substances.

EP-A-0 331 068 and WO 91/06 559 describe the use of polymerized immunoglobulins, especially IgG, to reduce specific interfering factors such as rheumatoid factors. However, not all non-specific interactions can be eliminated in a satisfactory manner. Further, the additional non-specific human immunoglobulins (monomeric or polymeric antibodies or their fragments) to the test for human antibodies can lead to an increase of the blank value. Moreover, the yield of human and animal IgG is complex and expensive.

It was, hence, an object of the invention to provide new interference-reducing substances where the reduction of non-specific interactions in immunoassays is improved as compared to prior art. Non-specific interactions are understood to be all interactions between components used in the methods that may lead to arroneous results. Interference-reducing substances should avoid false-positive analysis results, especially when antibodies are analyzed. It is a particular object to avoid interference when avidin or streptavidin are used as one of the binding partners in an immunoassay.

This object has been accomplished by means of avidin or streptavidin that has been inactivated with the aid of novel photo-activatable biotin derivatives. Surprisingly, the use of these substances led to a reduction of interference in immunoassays, especially in immunoassays where avidin or streptavidin were used as binding partners.

Subject matter of the invention are novel photo-activatable biotin derivatives of the formula I.

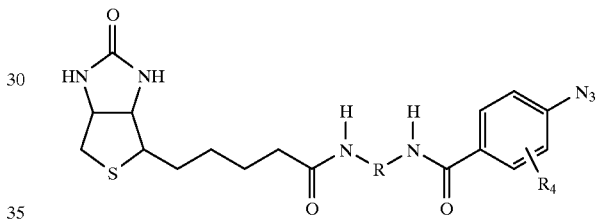

wherein R=[(CH$_2$)$_n$—O$_m$]$_q$—[(CH$_2$)$_r$—O$_s$]$_t$—(CH$_2$)$_p$
with n,r=2,3; m,s=0,1; q+t=1–4; p=1–4,
wherein the sum of all CH$_2$ groups does not exceed 10
and wherein R1 as a single or multiple substituent is hydrogen, C$_1$–C$_5$-alkyl, NH$_2$, COOH, F, Cl, or Br.

It is particularly preferred to have following insertion in the chain as R:

—(CH$_2$)$_3$—O—(CH$_2$)$_4$—O—(CH$_2$)$_3$—
—(CH$_2$)$_2$—O—(CH$_2$)$_2$—O—(CH$_2$)$_2$—
—(CH$_2$)$_{4-10}$—, particularly —(CH$_2$)$_4$— and —(CH$_2$)$_8$—

Another subject matter of the invention is the use of the photo-activatable biotin derivatives in accordance with the invention to inactivate streptavidin or avidin. The inactivation of streptavidin is accomplished in that the biotin derivatives of the invention are brought into contact with streptavidin or avidin. Owing to the very high binding affinity between streptavidin and biotin, biotin is bound to streptavidin. After saturation of the biotin binding sites with the biotin derivatives of the invention, the photoreaction is triggered to covalently attach biotin to the active center. In this process, the photo-activatable group of the biotin couples to the amino acid residue of the streptavidin molecule outside the active center thus binding the biotin tightly and covalently to the streptavidin receptor site. A possible photo source is, for example, a mercury vapor lamp with a wavelength ranging particularly between 250 and 450 nm. The time of exposure can range between 1 min and 10 h, preferably between 5 and 30 min.

Avidin or streptavidin are understood to be naturally occurring purified protein or recombinant avidin or streptavidin, or chemically modified derivatives thereof.

It is possible to use all derivatives of the native forms that are capable of binding free biotin or biotin that is covalently conjugated via the carboxyl group. These derivatives can also be obtained through chemical modification such as alkylation with alkyl halogenides, acetylation with carbonic acid chlorides or esters, oxidation of sugar residues (side chains) with periodates, for example, or by deleting individual amino acids or amino acid blocks within the primer sequence by means of enzymatic or recombinant methods. It is also possible to use oligomers or polymers of streptavidin/avidin (streptavidin may be mixed with avidin) obtained through chemical linking (e.g. by means of bifunctional linkers).

Subject matter of the invention are also inactivated avidin or streptavidin in accordance with the invention having the formula II immunoassays are particularly those where avidin or streptavidin are used as one of the binding components. Such immunoassays are known, for example from U.S. Don et al., J. Histochem. Cytochem. 27 (1979), 1131–1139 and Bayer and Wilchek, Analytical Biochemistry 171 (1988), 1–32. The interferences can be caused, for example, by antibodies to avidin or streptavidin as they may occur in human serum. The interference-reducing agent of the invention is, however, also advantageous in immunoassays where there is no avidin or streptavidin used. In these immunoassays, experience has shown the use of inactivated streptavidin which is bound to another molecule such as BSA or poly-BSA as particularly advantageous.

Another subject matter of the invention is an immunoassay for the determination of an analyte in a sample by means of

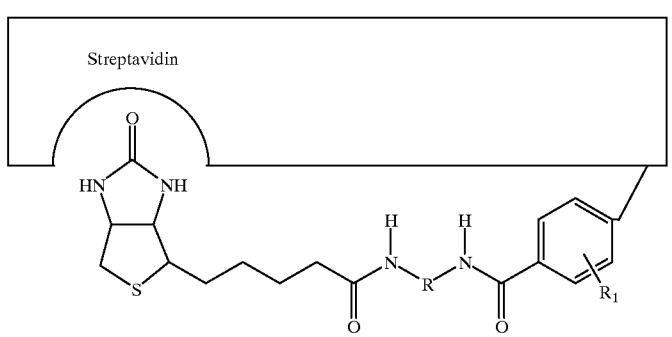

II wherein R and $R_1$ have the above given definition, wherein $R_1$ can in addition be $NO_2$ and wherein biotin is bound to the active center of streptavidin or avidin and in addition bound to streptavidin or avidin via a covalent binding outside the active center.

Photo-activatable biotin derivatives are known. EP-A-0 155 854 and EP-A-0 187 323 describe azide-substituted phenyls/nitrophenyls which are coupled to biotin via an amine-containing linker. A photoreactive biotin derivative of the formula 1. bringing the sample into contact with
   a) inactivated avidin or streptavidin of the formula II in accordance with the invention
   b) one or several specific binding partners of the analyte and
2. measuring the complex formed of analyte and specific binding partner as a measure for the presence of the analyte.

Possible analytes are all substances which react with at least one specific binding partner to form one specific

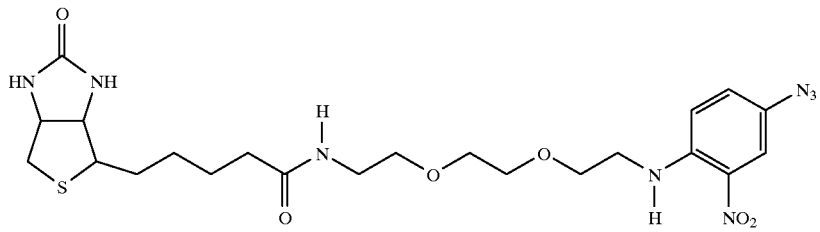

is described in the Boehringer Mannheim Biochemical Catalog, under the Id. Nos. 1292633 and 1292641.

These biotin derivatives are, however, only described for the labeling of DNA/RNA molecules, proteins in general and carbohydrates. A coupling especially to streptavidin is not described and would not be appropriate for the purpose of the labeling described in these references as streptavidin itself contains a binding site for biotin which renders a free labeling with biotin impossible.

Another subject matter of the invention is the use of the inactivated avidin or streptavidin in accordance with the invention to reduce interference in immunoassays. Inactivated avidin or streptavidin for reducing interference in complex such as haptens, antigens or antibodies. The method of the invention is particularly suitable for the detection of antibodies, especially auto-antibodies.

Samples are usually body fluids such as blood, plasma, serum, saliva, or urine.

Specific binding partners can be any biological or chemical binding partners that are able to specifically bind the analyte and to form a complex therewith. They include antibodies, antibody fragments, antigens, haptens, hormones, avidin, biotin, or derivatives thereof. In the present invention it is preferred to have antibodies or antigens or their fragments as binding partners of the analyte.

In order to detect the complex of analyte and specific binding partner, it is possible to use all conventional methods known to the expert in the field. It is possible to employ homogeneous methods where all binding partners are present in a soluble form, for example precipitation methods with turbidimetric or nephelometric determination of the formed complex, or immunoassays according to the CEDIA, EMIT or FPIA principles. Suitable are also heterogeneous methods where at least one reagent is bound to a solid phase. Examples include agglutination tests where one partner of the binding pair is bound to latex, for example, also sandwich assays, ELISA for the detection of specific antibodies or immunometric assays. Except for precipitation methods, all of these methods require that at least one of the specific binding partners be labeled. The label can directly supply a measurable signal, for example a radioisotopic, chemiluminescent, fluorescent, or electro-chemiluminescent label or a dyed particle such as a metal sol particle or dyed or undyed latex. The label can also supply an indirect signal, for example an enzymatic label such as peroxidase, glucose oxidase, β-galactosidase or alkaline phosphatase.

The immunoassays can also be carried out with the aid of test strips or biosensors, especially when one of the binding partners is coupled to the solid phase via streptavidin. Interference can also be reduced in plasmon resonance-based immunoassays.

Frequently, one reagent of the method for the detection of an analyte is coupled to the solid phase via a specific binding pair, such as avidin or streptavidin/biotin. The advantage involved is that the solid phase can be universally used in various other detection methods. It is also possible to bind the label via a specific binding pair through a component of the assay. It is, for example, possible to couple an enzyme to avidin or streptavidin and the binding partner, for example and antibody, can be biotinylated. Examples for such detection methods are known to the expert. The inactivated avidin or streptavidin of the invention is particularly suited for these cases.

When the method is carried out, the analyte is incubated with the individual test components and activated avidin or streptavidin and the immunoassay is then carried out. The concentration of the interference-reducing agent preferably ranges between 0.0001 and 1% (m/v), preferably between 0.01 and 1% (m/v).

The individual reaction components of the method for the detection of an analyte are advantageously offered in the form of a test combination or a test kit.

Another subject matter of the invention is, hence, a test kit for the detection of an analyte in a sample, comprising a) the inactivated avidin or streptavidin of the formula II of the invention and b) at least one specific binding partner of the analyte.

Moreover, the kit can also contain all other reagents such as buffer, detergents, labels, additives for the detection of the label such as enzyme substrates, solid phases and the like that are necessary to carry out the detection method. In a preferred manner, the interference-reducing agent and the one or several binding partners of the analyte are supplied in separate containers. It is, however, also possible to add the interference-reducing agent directly to the one or several binding partners of the analyte.

Another subject matter of the invention is a method for preparing the photo-activatable biotin derivatives of the formula I. The method is carried out such that biotin is coupled via its carboxyl functional groups to a primary or secondary amino group of a diamino compound by means of known condensation techniques. Subsequently, the free amino functional groups are bound to the photo-activatable group via another condensation reaction or substitution reaction (e.g. aromatic nucleophilic substituents). The scheme of synthesis can be reversed if desired.

EXAMPLE 1

Preparation of Photo-activatable Biotin
Synthesis of biotin-[8-(4-azidobenzoyl)amino-3,6-dioxaoctyl]amide (biotin-DADOO-AB) (4)

1.50 g (4 mmol) of biotinyl-1,8-diamino-3,6-dioxaoctane (biotin-DADOO, Boehringer Mannheim No. 1112074) are dissolved in 50 ml of freshly distilled DMF while stirring. Then, 1.04 g (4 mmol) of N-hydroxysuccinimidyl-(4-azidobenzoate) (HSAB, Boehringer Mannheim No. 1140051) and 0.55 ml (4 mmol) of trethylamine are successively added to the solution and stirred at 20° C. for 2 h. Subsequently, the solvent is removed in the rotation evaporator while an oil pump vacuum is applied. The remaining raw product is purified by means of chromatography on silica gel. To achieve this, the substance is dissolved in a minimum amount of chloroform/methanol 2/1 (v/v) while slightly heating up to 40° C. and the mixture is then applied on a silica gel 60 column (4×60 cm, manufactured by Merck). Then, elution is carried out with chloroform/methanol 2/1 (v/v) and the result is collected in 50 ml fractions. The fractions containing the pure product are then determined via TLC and purified (system described below). The solvent is removed on the rotation evaporator and the semi-solid residue is digested with approx. 50 ml diisopopyl ether. The fine crystalline colorless product is drawn off and dried overnight in a vacuum drying cabinet (0.1–0.15 bar/40° C.).

Yield: 1.24 g (60% d.Th.); TLC: Silic gel 60(Merck) $F_{254}$, chloroform/methanol 2/1 (v/v); $R_f$=0.71. $^1$H-NMR(100 MHz/$d_6$-DMSO): δ(ppm)=1.20–1.65(m, 6H); 2.07(tr, 2H); 2.60–3.65 (m, 15H); 4.05–4.20 (m; 2H); 6.38(d,br, 2H), 7.20 (d, 2H), 7.62 (tr,br, 2H); 7.91(d, 2H); 8.53 (tr,br, 2H). UV(CH$_3$OH): λ(max)=267 nm; IR(KBr): ν=2125 cm$^{-1}$
FIG. 1

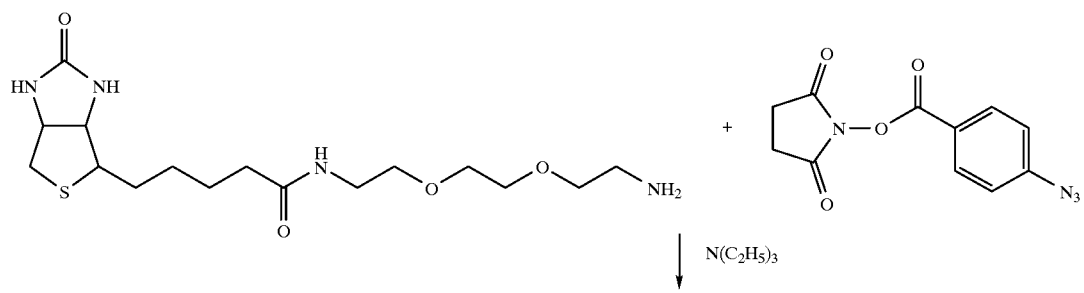

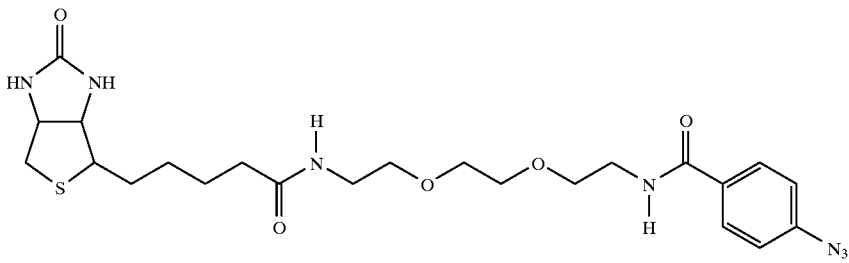

EXAMPLE 2

Preparation of Biotin

Principle:

Streptavidin is reacted with a photo-activatable biotin derivative (e.g. biotin-DADOO-AB) and dialysed in order to separate the free, non-bound biotin. The photoreaction is triggered by exposure to an Hg vapor lamp (350–700 nm) and the biotin is covalently linked to the binding center of streptavidin.

Procedure in Detail:

At a given protein concentration of 20 mg/ml in PBS buffer pH 7.5, a 10-fold molar excess of biotin-DADOO-AG reagent is added to 1 g of streptavidin (3.5 ml of a 25 mg/ml biotin-DADOO-AB stock solution in DMSO). Once the addition of reagent is completed, the mixture is stirred for 2 h at 25° C. in the dark.

Free, non-bound biotin derivative is completely separated (no longer detectable) in the dark by means of dialysis (20 h 4° C.) against a >500-fold volume of PBS buffer, pH 7.5. With a layer thickness of the solution of <5 cm, the mixture is exposed to an Hg vapor lamp (350–700 nm) under stirring over a period of 20 min and again dialysed against a >500-fold volume of PBS buffer, pH 7.5 (16–18 h, 4° C.).

EXAMPLE 3

Purification of Inactivated Streptavidin

Principle:

Inactivated streptavidin is purified from from streptavidin with remaining residual activity (biotin binding), from any remaining free biotin or from streptavidin to the surface to which biotin is covalently bound so as to be accessible at the surface (as opposed to the biotin linked in the binding pocket) by means of chromatography on an bovine serumalbumin/biotin and/or streptaviding adsorber on spherosil basis.

Procedure in Detail:

1 ml of streptavidin spherosil adsorber, equilibrated in PBS buffer, pH 7.5 is added to portions of 10 mg of protein in the reaction mixture and stirred for 2 h at room temperature. The adsorber is prepared according to conventional methods in that streptavidin is coupled to glutar dialydehyde-activated amino spherosil.

The suspension is transferred into a column and the column material is washed with PBS buffer pH 7.5. The protein contents is monitored at the end of the column via a UV monitor at $A_{280\ nm}$. The washing is continued until the solution is free of protein. The protein containing eluate is collected in a fraction.

1 ml of bovine serum albumin/biotin (PSA-Bi) sperosil adsorber, equilibrated in PBS buffer, pH 7.5 is added to the protein containing eluate of the streptavidin absorber for each portion of 10 mg of protein. This mixture is then stirred for 2 h at room temperature. The adsorber is prepared according to conventional methods in that BSA-Bi is coupled to glutar dialdehyde-activated amino sperosil. The suspension is transferred into a column and washed with PBS buffer, pH 7.5. The protein concentration is monitored at the end of the column via a UV monitor at $A_{280\ nm}$. The protein containing eluate contains the product and is collected in a fraction. The product (inactivated streptavidin) is concentrated down to 20 mg/ml of protein and lyophilized after filling.

EXAMPLE 4

Synthesis of biotin-[2-(4-azidobenzoyl) aminoethylamide (biotin-EDA-AB) 4a

N-(4-azidobenzoyl)ethylene diamine 2a 2.6 g (10 mmol) HSAB 1 are dissolved in 70 ml THF and dropwise added to a solution of 6.01 g (100 mmol) ethylene diamine in THF while stirring and cooling on ice. Subsequently, the ice bath is removed and the temperature is allowed to adjust to room temperature. The solvent is removed on the rotation evaporator and excess ethylene diamine is removed in a high vacuum as far as possible. The remaining raw product is purified by means of preparative column chromatography on silica gel 60 (manufactured by Merck; colum 4×68 cm, eluting agent: acetic ester/glacial acetic acid/water 6/3/1 (v/v/v)). The corresponding fractions are collected and concentrated. Product 2a is then taken up in approx. 100 ml methanol and becomes a slightly yellow solid material once the solvent is removed on the rotation evaporator.

Yield: 2.92 g (contains approx. 2–3 equivalents of $CH_3COOH$);

TLC: Silica gel 60 $F_{254}$ (Merck); acetic ester/glacial acetic acid/water 6/3/1 (v/v/v); $R_f$=0.49

Biotin-[2-(4-azidobenoyl)aminoethyl]amide 4a 1.03 g (5 mmol) of product 2a are suspended in 40 ml of distilled DMF and 1.4 ml triethylamine are added under stirring at 20° C. Subsequently, 1.17 g (5 mmol) biotin-N-hydroxysuccinimide ester (Boehringer Mannheim No. 734250) 3 and stirring is continued for another 3 h at 20° C. Then the solvent is removed on the rotation evaporator (oil pump vacuum, water bath 50° C.) and the concentrated residue is digested overnight with saturated $NaHCO_3$ solution. Product 4a is drawn off, washed with water and dried in an exsiccator.

Yield: 1.02 g (47% of theory) white to yellow powder;

TLC: Silica gel 60 $F_{254}$ (Merck); acetic ester/methanol 3/1 (v/v) +1% glacial acetic acid; $R_4$=0.31

$^1$H-NMR(100 MHz/$d_6$-DMSO): δ(ppm)=1.20–1.65(m, 6H); 2.08(tr, 2H); 2.60–3.45 (m, 7H); 4.05–4.20 (m; 2H); 6.40(d,br, 2H), 7.20 (d, 2H); 7.89(d, 2H); 7.90 tr,br, 1H); 8.49 (tr,br, 1H). UV($CH_3OH$): λ(max)=268 nm; IR(KBr): ν=2117 $cm^{-1}$

EXAMPLE 5

Synthesis of biotin-[2-(4-azidobenzoyl)aminohexyl] amide (biotin-HMDA-AB) 4b N-(4-azidobenzoyl)hexamethylendiamin 2b 2.6 g (10 mmol) HSAB 1 are dissolved in 70 ml THF and dropwise added to solution of 11.62 g (100 mmol) of hexamethylene diamine in THF under stirring and cooled on ice. Subsequently, the ice bath is removed and the temperature is allowed to adjust to room temperature. The solvent is drawn off on the rotation evaporator and excess hexymethylene diamine is removed in a high vacuum as far as possible. The remaining raw product is digested for 20 min in 100 ml of water and subsequently dried overnight in an exsiccator. Product 2b is a slightly yellow to brown solid material.

Yield: 2.09 g (80% of theory); TLC: Silica gel 60 $F_{254}$ (Merck); acetic ester/glacial acetic acid/water 6/3/1 (v/v/v); $R_f$=0.50

Biotin-[2-(4-azidobenzoyl)aminohexyl]amidE 4b 1.30 g (5 mmol) of product 2b are suspended in 40 ml of distilled DMF and 1.4 ml triethylamine are added under stirring at 20° C. Subsequently, 1.71 g (5 mmol) of biotin-N-hydroxysuccinimide ester 3 are added and stirring is continued for another 3 h at 20° C. Subsequently, the solvent is removed on a rotation evaporator (oil pump vacuum, water bath 50° C.) and the concentrated residue is digested overnight with saturated NaHCO$_3$ solution. Product 4b is drawn off, washed with water and dried in the exsiccator.

Yield: 1.71 g (70% of theory) white to yellow powder; TLC: Silica gel 60 $F_{254}$ (Merck); acetic ester/methanol 3/1 (v/v)+3% glacial acetic ester; $R_f$=0.38 $^1$H-NMR(100 MHz/ d$_6$-DMSO): δ(ppm)=1.20–1.75(m, 14H); 2.06(tr, 2H); 2.60–0.40 (m, 7H); 4.05–4.20 (m; 2H); 6.39(d,br, 2H); 7.19 (d, 2H); 7.73 (tr,br, 1H); 7.90(d, 2H); 8.44 (tr,br, 1H). UV(CH$_3$OH): λ(max)=267 nm; IR(KBr): ν=2121 cm$^{-1}$

EXAMPLE 6

Synthesis of N-[3-(4-azidobenzoyl)aminopropyl]-N-(3'-biotinoylaminopropyl)-methylamine acetate 4c (prior art according to EP-A-0 155 854)

N-(3-aminopropyl)-N-[3'-(4-azidobenzoyl)aminopropyl]-methylamine 2c 0.52 g (2 mmol) HSAB 1 are dissolved in 20 ml of THF and dropwise added to a solution of 0.52 g(2 mmol) N,N-bis-(3-aminopropyl)methylamine in 15 ml THF under stirring and while cooled on ice. Subsequently, the ice bath is removed and the temperature is allowed to adjust to room temperature. The solvent is drawn off on a a rotation evaporator and excess N,N-bis-(3-aminopropyl) methylamine is removed in a high vacuum as far as possible while heating up the piston. The remaining raw product is digested for 20 min in 100 ml of ether and subsequently purified via column chromatography on silica gel 60 (4×68 cm; eluent: chloroform/methanol/ammonia 2/2/1 (v/v/v). The corresponding fractions are collected, the solvent is removed and the remaining product 2c is dried for several hours in a high vacuum.

Yield: 380 mg (66% of theory) slightly yellow to brown oil; TLC: Silica gel 60 $F_{254}$ (Merck); chloroform/methanol/ ammonia 2/2/1 (v/v/v); $R_f$=0.82

N-[3-(4-azidobenzoyl)aminopropyl]-N-(3'-biotinoylaminopropyl)-methylamine acetate 4c 290 mg (1 mmol) of product 2c are dissolved in 25 ml of freshly distilled DMF and 0.17 ml of triethylamine nad 342 mg (1 mmol) biotin N-hydroxysuccinimide ester 3 are added. The solution is stirred for 1 h at 20° C. and subsequently concentrated in a high vacuum. The raw product is purified via colum chromatography on silica gel 60 (6×45 cm; eluent: acetic ester/glacial acetic acid/water 5/5/2 (v/v/ v)). The corresponding fractions are combined and the solvent mixture is removed on the rotation evaporator. The oily residue is dissolved in methanol, concentrated and digested with diisopropyl ether. Subsequently, product 4c is dried for at least 6 h in a high vacuum.

Yield: 405 mg (70% of theory) of viscous, slightly yellow to brown oil; TLC: Silica gel 60 $F_{254}$ (Merck); chloroform/ methanol/ammonia 5/5/2 (v/v/v); $R_f$=0.38

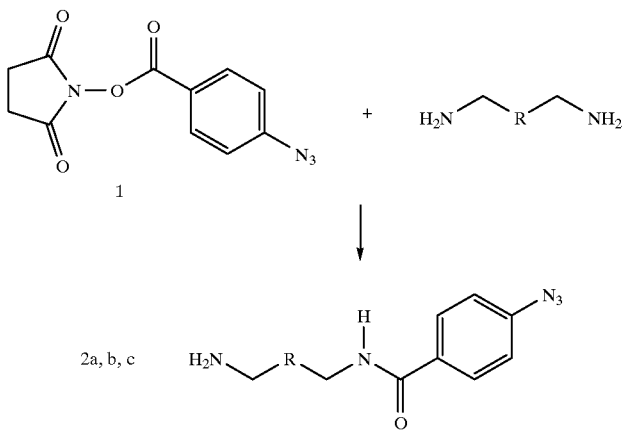

-continued

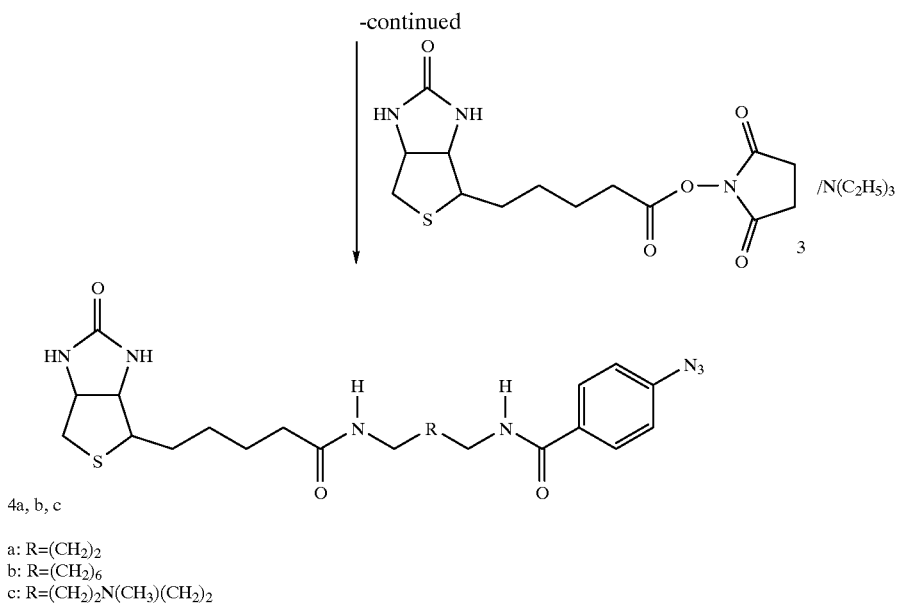

4a, b, c a: R=(CH$_2$)$_2$
b: R=(CH$_2$)$_6$
c: R=(CH$_2$)$_2$N(CH$_3$)(CH$_2$)$_2$

EXAMPLE 7

Reducing the Interference of an HCV Test with biotin(photo-activated)-SA

Test Principle:
2-step sandwich assay with streptavidin solid phase (procedure and reagents as provided in the Enzymun-Testo® Anti-HIV)
Step 1: Biotinlated peptides plus sample
Step 2: Reaction of the wall-bound antibodies with an anti-human IgG POD conjugate
Step 3: Indicator reaction with ABTSO® as substrate
Incubation Buffer:
Na phosphate 40 mmol/l, pH 7.4
NaCl 7.1 g/l
Preservative
Plasma diagnostic-based 200 g/l
HCV peptides from the core, NS4 and NS5 regions
±inactivated streptavidin according to examples 1 and 2
Conjugate Buffer:
Na phosphate 40 mmol/l, pH 7.4
NaCl 7.1 g/l
Prefervative
Bovine serum albumin 1 g/l
Bovine IgG 4 g/l
Triton×100 1 g/l
Anti-human IgG POD 15 U/l
Incubation Times:
Step 1: 1 h (sample+incubation buffer)
Step 2: 1 h (+conjugating buffer)
Step 3: 1 h (substrate reaction with ABTS)
Samples:
3 negative serum samples (reference 1)
6 false-positive anti-HCV negative samples
3 positive anti-HCV samples (reference 2)
Volumes:
Sample 20 µl
all other reagents 500 µl each
Procedure:
Carried out on the ES 600 instrument 16 25° C.
Substrate Measurement:
Substrate solution is measured at 422 nm on the ES 600 instrument (manufactured by Boehringer Mannheim GmbH)

The absorbances are given in Table 1.

| Samples | Without inactivated SA in incubating buffer | 20 µg/ml inactivated SA in incubating buffer | Signal decrease after addition of inactivated SA |
|---|---|---|---|
| Negative serum 1 | 0.036 | 0.027 | * |
| Negative serum 2 | 0.042 | 0.035 | * |
| Negative serum 3 | 0.078 | 0.076 | * |
| HCV negative serum 1 | 0.528 | 0.125 | 76% |
| HCV negative serum 2 | 0.467 | 0.106 | 77% |
| HCV negative serum 3 | 0.979 | 0.161 | 84% |
| HCV negative serum 4 | 0.499 | 0.094 | 81% |
| HCV negative serum 5 | 2.049 | 0.471 | 77% |
| HCV negative serum 6 | 0.427 | 0.065 | 85% |
| HCV positive serum 1 | 1.747 | 1.645 | 6% |
| HCV positive serum 2 | 1.161 | 1.076 | 7% |
| HCV positive serum 3 | 1.104 | 1.026 | 7% |

*No data available since the signal generated is too low.

EXAMPLE 8

Comparison of Various Streptavidins Inactivated with Various Photo-activatable Biotins Streptavidin is inactivated with photo-activatable biotins according to examples 4, 5 and 6. A comparison of the results is given in example 7. The streptavidin reagents prepared with Bi-HMD-(HS) AB and Bi-D ADOO (HS) AB show a significantly increased interference-reducing effect as compared to the streptavidin obtained with a biotin derivative according to prior art.

| Samples | Without inactivated SA in incubating buffer | Signal decrease after addition of 0.05 mg/ml SA inactive in incubating buffer | | |
| --- | --- | --- | --- | --- |
| | | Bi-HMD-(HS)AB | Bi-DADOO-(HS)AB | Bi-DAPMA-(HS)AB |
| Neg. serum 1 | 1.237 | 95% | 96% | 50% |
| Neg. serum 2 | 0.163 | 46% | 50% | 10% |
| Pos. serum 1 | 3.945 | 10% | 9% | 12% |

We claim:

1. An inactivated avidin or streptavidin of formula II

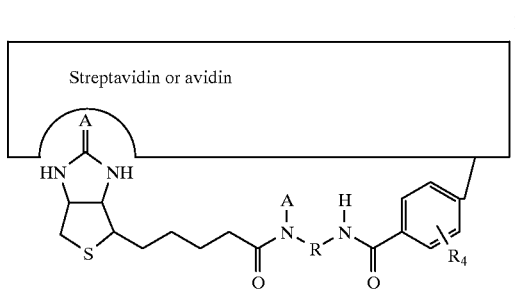

II wherein

R=[(CH$_2$)$_n$—O$_m$]$_q$—[(CH$_2$)$_r$—O$_s$]$_t$—(CH$_2$)$_p$, wherein n, r=2, 3 or 4; m,s=1; q+t=1–4; and p=1–4, and the sum of all CH$_2$ groups in R does not exceed 10; and R$_1$ is at least one ring substituent selected from the group consisting of hydrogen, C$_1$–C$_5$ alkyl, NH$_2$, COOH, NO$_2$, F, Cl and Br, produced by a process comprising:
(a) providing a photo-activatable biotin derivative of formula I

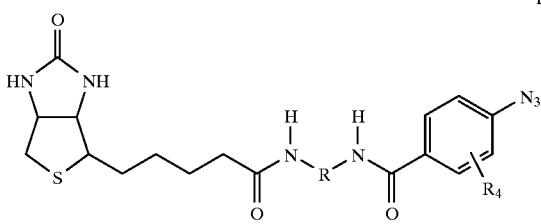

I wherein R and R$_1$ are as defined above; and
(b) contacting the biotin derivative with avidin or streptavidin

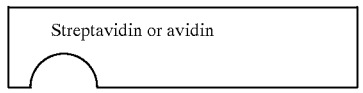

wherein "

" represents the active center of the avidin or streptavidin, and triggering a photoreaction, to specifically bind the biotin derivative to the active center of the avidin or streptavidin via the

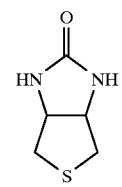

group,
and to covalently bind the biotin derivative to the avidin or streptavidin outside the active center via the photo-activatable N3 group.

2. A complex comprising avidin or streptavidin having bound thereto a photo-activatable biotin derivative, wherein the complex is of formula II

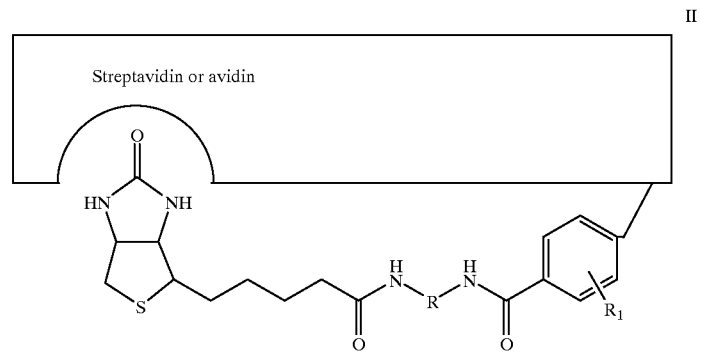

II wherein
R=[(CH$_2$)$_n$—O$_m$]$_q$—[(CH$_2$)$_r$—O$_s$]$_t$—(CH$_2$)$_p$, wherein n, r=2, 3 or 4; m,s=1; q+t=1–4; and p=1–4, and the sum of all CH$_2$ groups in R does not exceed 10, R$_1$ is at least one ring substituent selected from the group consisting of hydrogen, C$_1$–C$_5$ alkyl, NH$_2$, COOH, NO$_2$, F, Cl and Br, and "

" represents the active center of the avidin or streptavidin which is specifically bound by the biotin derivative via the

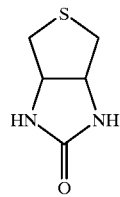

group, and wherein the biotin derivative is covalently bound to the avidin or streptavidin outside the active center via a photo-activatable group.

3. A method for the immunological determination of an analyte in a sample comprising the following steps:
   a) contacting the sample which may contain the analyte with inactivated streptavidin or avidin of claim 1;
   b) contacting the sample with at least one specific binding partner of the analyte to form a complex, wherein step a) and step b) can occur in any order or simultaneously; and
   c) measuring the formed complex of analyte and specific binding partners as a measure of the presence of the analyte.

4. A method of reducing interference in an immunoassay which requires the formation of a complex between an analyte and a specific binding partner of the analyte, comprising conducting the immunoassay in the presence of the inactivated streptavidin or avidin of claim 1.

5. A method for the immunological determination of an analyte in a sample comprising the following steps:
   a) contacting the sample which may contain the analyte with inactivated streptavidin or avidin of claim 2;
   b) contacting the sample with at least one specific binding partner of the analyte to form a complex, wherein step a) and step b) can occur in any order or simultaneously; and
   c) measuring the formed complex of analyte and specific binding partners as a measure of the presence of the analyte.

6. A method of reducing interference in an immunoassay which requires the formation of a complex between ah analyte and a specific binding partner of the analyte, comprising conducting the immunoassay in the presence of the inactivated streptavidin or avidin of claim 2.

7. The method of claim 3, wherein the immunoassay further comprises the use of the specific binding pair avidin/biotin or streptavidin/biotin.

8. The method of claim 5, wherein the immunoassay further comprises the use of the specific binding pair avidin/biotin or streptavidin/biotin.

9. The method of claim 4, wherein streptavidin or avidin is also used as a binding partner in the immunoassay.

10. The method of claim 6, wherein streptavidin or avidin is also used as a binding partner in the immunoassay.

11. Test kit for the determination of an analyte comprising, in separate containers:
    a) inactivated streptavidin or avidin of claim 2, and
    b) at least one specific binding partner of the analyte.

12. A photo-activatable biotin derivative of formula I

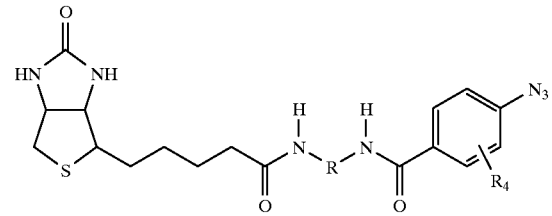

wherein R=—[(CH$_2$)$_n$—O$_m$]$_q$—[(CH$_2$)$_r$—O$_s$]$_t$—(CH$_2$)$_p$—
wherein n and r are each independently=2, 3 or 4; m and s are each independently=1; q+t=1–4; and p=14;
wherein the sum of all CH$_2$ groups in R does not exceed 10;
and wherein R$_1$ is at least one ring substituent selected from the group consisting of hydrogen, C$_1$–C$_5$-alkyl, NH$_2$, COOH, F, Cl, and Br.

13. The biotin derivative of claim 12, wherein n=3, r=4, m,s=1, q,t=1, p=3.

14. The biotin derivative of claim 12, wherein n,r=2, m,s=1, q,t=1, p=2.

15. Test kit for the determination of an analyte comprising, in separate containers:
    a) inactivated streptavidin or avidin of claim 1, and
    b) at least one specific binding partner of the analyte.

16. A method for the preparation of a photo-activatable biotin derivative of claim 12, comprising:
    a) attaching a diamino compound of the formula III

NH$_2$—R—NH$_2$ (III)

wherein R=[(CH$_2$)$_n$—O$_m$]$_q$—[(CH$_2$)$_r$—O$_s$]$_t$—(CH$_2$)$_p$
    wherein n,r=2,3; m,s=1; q+t=1–4; p=1–4;
    wherein the sum of all CH$_2$ groups in R does not exceed 10;
    1) at one end to the carboxyl group of biotin and
    2) at the other end to a photo-activatable group having the formula

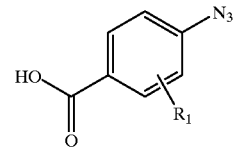

wherein R$_1$ is at least one ring substituent selected from the group consisting of hydrogen, C$_1$–C$_5$-alkyl, NH$_2$, COOH, F, Cl, and Br.

17. A method for inactivating streptavidin or avidin with a photo-activatable biotin derivative comprising:
    a) contacting the avidin or streptavidin with the biotin derivative, and
    b) coupling the avidin or streptavidin and the biotin by exposure to radiation,
    wherein the biotin derivative is a compound of claim 12.

* * * * *

UNITED STATES PATENT AND TRADEMARK OFFICE
CERTIFICATE OF CORRECTION

PATENT NO. : 5,952,185
DATED : September 14, 1999
INVENTOR(S) : Huber, et. al.

It is certified that error appears in the above-identified patent and that said Letters Patent is hereby corrected as shown below:

Title page, item [63], please add after "abandoned" -- which is a 371 of PCT/EP95/00690 February 25, 1995.--.

Signed and Sealed this

Thirtieth Day of May, 2000

Attest:

Q. TODD DICKINSON

Attesting Officer

Director of Patents and Trademarks